United States Patent
Mukarram et al.

(10) Patent No.: US 7,291,735 B2
(45) Date of Patent: Nov. 6, 2007

(54) PROCESS FOR THE MANUFACTURE OF (+)-(S)-CLOPIDOGREL BISULFATE FORM-1

(75) Inventors: Mohammed Siddiqui Jaweed Mukarram, Aurangabad (IN); Yekanathsa Aravind Merwade, Aurangabad (IN); Reyaz Anjum Khan, Aurangabad (IN)

(73) Assignee: The Company of Wockhard Limited

( * ) Notice: Subject to any disclaimer, the term of this patent is extended or adjusted under 35 U.S.C. 154(b) by 11 days.

(21) Appl. No.: 10/564,364

(22) PCT Filed: Aug. 4, 2003

(86) PCT No.: PCT/IB03/03104

§ 371 (c)(1),
(2), (4) Date: Feb. 23, 2006

(87) PCT Pub. No.: WO2005/012300

PCT Pub. Date: Feb. 10, 2005

(65) Prior Publication Data

US 2006/0183907 A1 Aug. 17, 2006

(51) Int. Cl.
*C07D 471/02* (2006.01)
(52) U.S. Cl. ..................................................... 546/114
(58) Field of Classification Search ................. 546/114
See application file for complete search history.

(56) References Cited

U.S. PATENT DOCUMENTS 6,429,210 B1 * 8/2002 Bousquet et al. ........... 514/301

* cited by examiner

*Primary Examiner*—D. Margaret Seaman
*Assistant Examiner*—Nizal S. Chandrakumar
(74) *Attorney, Agent, or Firm*—Bio Intellectual Property Services (Bio IPS) LLC; O. M. (Sam) Zaghmout

(57) ABSTRACT

The present invention relates to a novel process for the manufacture of blood-platelet aggregation inhibiting agent. In particular, the present invention is directed to a process for the manufacture of Methyl-(+)-(S)-α-(2-chlorophenyl)-6,7-dihydrothieno [3,2-c]pyridine-S-(4H)acetate bisulfate Form-I.

3 Claims, No Drawings

PROCESS FOR THE MANUFACTURE OF (+)-(S)-CLOPIDOGREL BISULFATE FORM-1

FIELD OF THE INVENTION

The present invention relates to a novel process for the manufacture of blood-platelet aggregation inhibiting agent. In particular, the present invention is directed to a process for the manufacture of Methyl-(+)-(S)-α-(2-Chlorophenyl)-6,7-dihydrothieno[3,2-c]pyridine-5(4H)-acetate bisulfate Form-I of Formula:

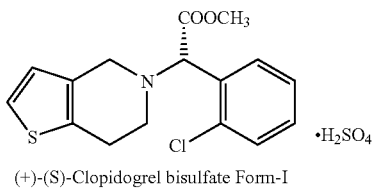

(+)-(S)-Clopidogrel bisulfate Form-I

BACKGROUND OF THE INVENTION

Clopidogrel is an inhibitor of platelet aggregation. Clopidogrel's platelet inhibiting activity makes it an effective drug for reducing the induce of ischemic strokes or heart attacks. By inhibiting platelet aggregation, Clopidogrel reduces the chance of arterial blockage, thus preventing strokes and heart attacks. Recent studies have shown that Clopidogrel is more effective in blocking platelet aggregation than Aspirin. Clopidogrel is much effective than Aspirin even at much lower dosage. In addition to being more effective, Clopidogrel produces much less gastrointestinal bleeding than Aspirin.

European patent 281459 describes the enantiomers of tetrahydrothieno pyridine derivatives and their pharmaceutically acceptable salts. The patent specifically claims Clopidogrel hydrogen sulfate, i.e., the dextrorotatory isomer which posses an excellent platelet aggregation inhibiting activity whereas the levo-rotatory isomer is less active. EP 281459 makes no reference to existence of the specific polymorphic forms of clopidigrel hydrogen sulfate.

Dextro-rotatory isomer of Clopidogrel is prepared by salt formation from the racemic compound using an optically active acid such as 10-L-camphorsulphonic acid in acetone, followed by successive re-crystallization of the salt until a product with constant rotatory power is obtained, followed by release of dextro-rotatory, isomer from its salt by a base. Clopidogrel hydrogen sulfate is then obtained in standard manner by the dissolution of said base in acetone cooled in ice and addition of concentrated sulfuric acid to precipitation. The precipitate thus obtained is then isolated by filtration, washed and dried to give Clopidogrel hydrogen sulfate in the form of white crystals. U.S. Pat. Nos. 4,874,265; 5,132,435; 6,258,961, 6,215,005 and 6,180,793 describe methods that can be used to prepare Clopidogrel hydrogen sulfate.

Clopidogrel bisulfate Form I and II was first time disclosed in International Publication No. WO 99/65915, though Form-I is originally disclosed in EP 281459. U.S. Pat. Nos. 6,429,210; 6,504,030 and US patent application 2002/019829 A1 disclose the manufacturing process of Clopidogrel hydrogen sulfate Form-I and II. These polymorphs are prepared by dissolving Clopidogrel camphor sulfate in acetone followed by addition of conc. Sulfuric acid at an ambient temperature. Excess of acetone is distilled and residue is cooled down to 0-5° C. followed by filtration to get Clopidogrel Form-I. The Form-II of Clopidogrel is obtained from residual mother liquor after 3-6 months period. These US patents does not disclose a process for the manufacture of Form-I only and hence, there is huge loss in the yield of Clopidogrel hydrogen sulfate Form-I. US patent application 2003/0114479 discloses the manufacturing processes for Clopidogrel hydrogen sulfate Form-I, II, III, IV, V and amorphous forms. The application also claims the preparation of Clopidogrel hydrogen sulfate Form-I from amorphous Clopidogrel hydrogen sulfate. Specification of the US patent application 2003/0114479 discloses the preparation method of Clopidogrel hydrogen sulfate Form-I using different combinations of alcohol and ether in 56-88% yield.

PRESENT INVENTION

The present invention relates to a novel process for the preparation of Clopidogrel bisulfate or the bisulfate of methyl-(+)-(S)-α-(2-chlorophenyl)-4,5,6,7-tetrahydrothieno[3,2,-c]pyridine-5-acetate. More particularly, the invention relates to a novel process for the preparation of Clopidogrel bisulfate Form-1 having Formula:

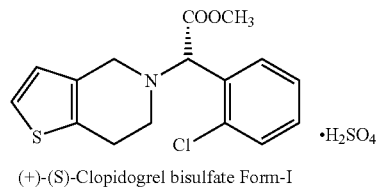

(+)-(S)-Clopidogrel bisulfate Form-I

Single solvent like isopropyl alcohol, isopropyl ether, 2-butanol etc. afforded mixture of Form-I and Form-II as evidenced by IR and XRD values. Even using seeded crystals of pure Form-I in acetone afforded only (+)-(S)-Clopidogrel bisulfate Form-II.

It is observed that ethyl acetate is the solvent of choice for getting (+)-(S)-Clopidogrel bisulfate Form-I in good yield and highly pure form. The Form-I of Clopidogrel bisulfate is well characterized by IR and XRD. These values are identical with the reported values of Form-I (reported in U.S. Pat. No. 6,429,210 B1). HPLC purity of Clopidogrel bisulfate Form-I prepared using ethyl acetate solvent is found more than 99%. An increase in melting point is observed in our process, i.e., 198 to 200° C. in comparison to 181.2° C. disclosed in U.S. Pat. No. 6,429,210 B1. The increase in melting point indicates higher purity of Form-I from what is reported in the "210" patent.

The present process for the manufacture of Clopidogrel bisulfate in an ester solvent, more specifically in ethyl acetate consumes less time than other solvent combinations reported in the prior art. It is also observed that the yield and purity of the Form-I is 88% and 99%, respectively. The obtained yield and purity of the Form-I by this process is better than reported in prior art. The specific rotation $[\alpha]_D^{20}$ of the Clopidogrel bisulfate Form-I is observed at +55.16° at a concentration of 1.61 gm/100 ml methanol. Clopidogrel bisulfate is characterized by $^1$H NMR, $^{13}$C NMR, mass and CHN analyses. The (+)-(S)-Clopidogrel bisulfate Form-I is confirmed on the basis of IR, XRD and melting point analyses. These values are tabulated as follows. For comparison purpose the values of Form-II are also given in the table.

IR, XRD, HPLC purity, melting point and Specific Rotation of (+)-(S)-Clopidogrel bisulfate Form-I and Form-II are tabulated as follows:

TABLE

Comparative analytical data of (+)-(S)-Clopidogrel bisulfate Form-I and Form-II.

| Sr. No. | Analysis | (+)-(S)-Clopidogrel bisulfate Form-I | (+)-(S)-Clopidogrel bisulfate Form-II |
|---|---|---|---|
| 1. | IR | 2987, 1753, 1222, 1175, 841 cm$^{-1}$ | 2551, 1497, 1189 and 1029 cm$^{-1}$ |
| 2. | XRD | 9.60, 8.13, 5.80, 4.95, 4.80, 4.31, 3.86, 3.83, 3.8, 3.49 d(A°) | 10.04, 6.86, 6.49, 5.66, 5.01, 4.80, 4.11, 3.87, 3.74, 3.60 d(A°) |
| 3. | HPLC Purity | 99.96% | 99.94% |
| 4. | Melting Point | 198-200° C. | 176-178° C. |
| 5. | Specific Rotation (c = 1.68% in methanol) | +55.16° | +55.10° |

Form-I obtained by this process is found to be stable and does not convert to any other forms.

Apart from all these technical and economical advantages of the process according to the invention, excellent yields and very good quality of the desired product, viz., Clopidogrel bisulfate Form-I is obtained. The process is suitable for industrial scale.

The following example illustrates the invention more clearly, without limiting its scope.

EXAMPLES

The following examples illustrate the invention, but is not limiting thereof.

Preparation of (+)-(S)-Clopidogrel Bisulfate Form-I (a) Resolution of (+)-(S)-Clopidogrel Racemic Clopidogrel base 12 gm (0.037 mole) (prepared according to procedure described in U.S. Pat. No. 4,529, 596) is dissolved in acetone (100 ml) and to it at 20° C. a solution of L-camphor-10-sulphonic acid, 5.196 gm (0.037 mole) in 20 ml acetone is added drop-wise. The mixture is heated at reflux temperature for 7 to 8 hours and then cooled to room temperature. The mixture is seeded with (+)-(S)-Clopidogrel-camphor-sulfonate salt (2.5% of the weight of base), stirred at room temperature for 10-12 hours. The product is filtered under suction to get (+)-(S)-Clopidogrel-camphor-sulfonate salt and washed with acetone which yielded 5.20 gm of product. The (+)-(S)-Clopidogrel is characterized on the basis of specific rotation based on literature and $[\alpha]_D^{20}$ of (+)-(S)-Clopidogrel is found +24.70° at a concentration of 1.68 gm/100 ml methanol. The 5.20 gm of the above compound is treated with minimum amount of water and made alkaline with sodium bicarbonate at 5° C., the obtained mixture is extracted in dichloromethane and subsequently removal of the solvent provided oily (+)-(S)-Clopidogrel in 4.92 gm yield and 99.96% pure form based on HPLC.

The structure of the (+)-(S)-Clopidogrel has been assigned on the basis of spectral values like $^1$H NMR, $^{13}$C NMR and specific rotation etc.

(b) (+)-(S)-Clopidogrel bisulfate Form-I (+)-(S)-Clopidogrel, 4.50 gm (0.0139 mole) is dissolved in ethyl acetate 50 ml and seeded with (+)-(S)-Clopidogrel bisulfate Form-I (2.5% of the weight of base). During stirring Conc. sulfuric acid 1.50 gm (0015 mole) is added at room temperature. After complete addition the reaction slurry is heated at reflux for 1 hour. Then it is stirred at room temperature for 1 hour. The product is then filtered under suction and washed with ethyl acetate followed by drying under vacuum at 60 to 70° C. for 6-8 hours. After complete drying, 4.0 gm (+)-(S)-Clopidogrel bisulfate Form-I is obtained in having 99.96% purity and $[\alpha]D^{20}$=+51.16° at a concentration of 1.61 gm/100 ml methanol.

The (+)-(S)-Clopidogrel bisulfate Form-I is characterized by $^1$H NMR, $^{13}$C NMR, mass and CHN analyses. The Form-I of (+)-(S)-Clopidogrel bisulfate has been confirmed on the basis of IR, XRD and melting point etc.

We claim:

1. The Form-I of clopidogrel bisulfate having a melting point of 198° C. to 200° C.

2. The Form-I of clopidogrel bisulfate of claim 1, wherein the clopidogrel bisulfate has a purity of more than 99% by HPLC.

3. The Form-I of clopidogrel bisulfate of claim 2, wherein the clopidogrel bisulfate has a purity of more than 99.96%.

* * * * *

UNITED STATES PATENT AND TRADEMARK OFFICE
CERTIFICATE OF CORRECTION

| | |
|---|---|
| PATENT NO. | : 7,291,735 B2 |
| APPLICATION NO. | : 10/564364 |
| DATED | : November 6, 2007 |
| INVENTOR(S) | : Mukarram et al. |

It is certified that error appears in the above-identified patent and that said Letters Patent is hereby corrected as shown below:

Title Page, item [75]

In the name of the first inventor:

"Mohammed Siddiqui Jaweed Mukarram"
-- Mohammed Jaweed Mukarram Siddiqui --

Signed and Sealed this

Twenty-second Day of January, 2008

JON W. DUDAS
*Director of the United States Patent and Trademark Office*